(12) United States Patent
Nold et al.

(10) Patent No.: US 11,078,264 B2
(45) Date of Patent: Aug. 3, 2021

(54) INHIBITING GRANULOCYTE MACROPHAGE-COLONY STIMULATING FACTOR (GM-CSF) PREVENTS PRETERM BIRTH

(71) Applicant: UNIVERSITY OF CONNECTICUT, Farmington, CT (US)

(72) Inventors: Christopher Nold, Glastonbury, CT (US); Anthony Vella, Simsbury, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 16/655,733

(22) Filed: Oct. 17, 2019

(65) Prior Publication Data
US 2020/0123246 A1    Apr. 23, 2020

Related U.S. Application Data

(60) Provisional application No. 62/746,626, filed on Oct. 17, 2018.

(51) Int. Cl.
*C07K 16/24* (2006.01)
*A61P 15/06* (2006.01)
*A61K 39/00* (2006.01)
*A61K 38/16* (2006.01)
*C12N 15/113* (2010.01)

(52) U.S. Cl.
CPC ............ *C07K 16/243* (2013.01); *A61K 38/16* (2013.01); *A61P 15/06* (2018.01); *C12N 15/1136* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,867,495 B2 | 1/2011 | Steidl et al. |
| 8,017,748 B2 | 9/2011 | Raum et al. |
| 8,263,075 B2 | 9/2012 | Cohen et al. |
| 8,506,960 B2 | 8/2013 | Cohen et al. |
| 9,453,050 B2 | 9/2016 | Kaminska-Kaczmarek et al. |
| 2014/0335081 A1 | 11/2014 | Godwood et al. |

OTHER PUBLICATIONS

Kumar et al., 17α-hydroxyprogesterone caproate is not an optimal progestogen for inhibition of in-vitro fetal membrane weakening. Reproductive Sciences, (Mar. 2017) vol. 24, No. 1, Supp. 1, p. 113A. Abstract No. T-028 (Year: 2017).*
Cook et al.; "Blockage of Collagen-induced Arthritis Post-onset by Antibody to Granulocyte-macrophage Colony-Factor (GM-CSF): Requirement for GM-CSF in the Effector Phase of Disease"; Arthritis Res; 3; pp. 293-298; (2001).
Nold et al.; "Block of Granulocyte-Macrophage Colony-Stimulating Factor Prevents Inflammation-Induced Preterm Birth in a Mouse Model for Parturition"; Reproductive Sciences; 26(4); pp. 551-559; (2019).
Poster Presentation at the Society for Maternal Fetal Medicine 38th Annual Pregnancy Meeting, Dallas, Texas, Jan. 29-Feb. 3, 2018.
Yang et al.; "Dependence of Interleukin-1-Induced Arthritis on Granulocyte-Macrophage Colony-Stimulating Factor"; Arthritis & Rheumatism; 44(1); pp. 111-119; (2001).
McQualter et al.; "Granulocyte Macrophage Colony-stimulating Factor: A New Putative Therapeutic Target in Multiple Sclerosis"; J. Exp. Med.194(7); pp. 873-881 (2001).
Chandiramani, M. et al.; "Limited Relationship between Cervico-Vaginal Fluid Cytokine Profiles and Cervical Shortening in Women at High Risk of Spontaneous Preterm Birth"; PLOS One, vol. 7, Issue No. 12; 2012; e52412; doi:10.1371/journal.pone.0052412.
Curry, A. et al.; "First trimester maternal plasma cytokine levels, pre-pregnancy body mass index, and spontaneous preterm delivery"; Acta Obstetricia et Gynecologia, vol. 88; 2009; pp. 332-342.
Elovitz, M. et al.; "Animal Model: A New Model for Inflammation-Induced Preterm Birth—The Role of Platelet-Activating Factor and Toll-Like Receptor 4"; American Journal of Pathology, vol. 163, Issue No. 5; 2003; pp. 2103-2111.
Elovitz, M. et al.; "Animal models of preterm birth"; Trends in Endocrinology and Metabolism, vol. 15, Issue No. 10; 2004; pp. 479-487.
Elovitz, M. et al.; "Can medroxyprogesterone acetate alter Toll-like receptor expression in a mouse model of intrauterine inflammation?"; American Journal of Obstetrics & Gynecology, vol. 193; 2005; pp. 1149-1155; doi:10.1016/j.ajog.2005.05.043.
Elovitz, M. et al.; "Medroxyprogesterone acetate modulates the immune response in the uterus, cervix and placenta in a mouse model of preterm birth"; The Journal of Maternal-Fetal & Neonatal Medicine, vol. 21, Issue No. 4; 2008; pp. 223-230; doi:10.1080/14767050801923680.
Elovitz, M. et al.; "The use of progestational agents for preterm birth: Leesons from a mouse model"; American Journal of Obstetrics & Gynecology, vol. 195; 2006; pp. 1004-1010; doi:10.1016/j.ajog.2006.06.013.
Kacerovsky, M. et al.; "Amniotic Fluid Protein Profiles of Intraamniotic Inflammatory Response to *Ureaplasma* spp. and Other Bacteria"; PLOS One, vol. 8, Issue No. 3; 2013; e60399; doi:10.1371/journal.pone.0060399.
Kemp, M. et al.; "Preterm Birth, Infection, and Inflammation Advances From the Study of Animal Models"; Reproductive Sciences, vol. 17, Issue No. 7; 2010; pp. 619-628; doi:10.1177/1933719110373148.

(Continued)

*Primary Examiner* — Elly-Gerald Stoica
(74) *Attorney, Agent, or Firm* — Cantor Colburn LLP

(57) ABSTRACT

A method of treating a pregnant female subject includes administering to the pregnant female subject an effective amount of a Granulocyte Macrophage-Colony Stimulating Factor (GM-CSF) inhibitor, wherein the effective amount of the GM-CSF inhibitor is effective to reduce, prevent or delay preterm birth.

12 Claims, 7 Drawing Sheets

Specification includes a Sequence Listing.

(56) References Cited

OTHER PUBLICATIONS

Kumar, D. et al.; "Decidual GM-CSF is a critical common intermediate necessary for thrombin and TNF induced in-vitro fetal membrane weakening"; Placenta, vol. 35; 2014; pp. 1049-1056; DOI: http://dx.doi.org/10.1016/j.placenta.2014.10.001.
Norwitz, E. et al.; "The Control of Labor"; New England Journal of Medicine, vol. 341, Issue No. 9; 1999; pp. 560-666; doi:10.1056/NEJM199908263410906.
Romero, R. et al.; "Preterm Labor: One Syndrome, Many Causes"; Science, vol. 345, Issue No. 6198; 2014; pp. 160-765; doi:10.1126/science.1251816.
Sharma, A. et al.; "Granulocyte macrophage colony stimulating factor (GM-CSF), the critical intermediate of inflammation-induced fetal membrane weakening, primarily exerts its weakening effect on the choriodecidua rather than the amnion"; Placenta, vol. 89; 2020; pp. 1-7; DOI: https://doi.org/10.1016/j.placenta.2019.10.003.

\* cited by examiner

INHIBITING GRANULOCYTE MACROPHAGE-COLONY STIMULATING FACTOR (GM-CSF) PREVENTS PRETERM BIRTH

CROSS-REFERENCE TO RELATED APPLICATIONS

This application claims priority to U.S. Provisional Application 62/746,626 filed on Oct. 17, 2018, which is incorporated herein by reference in its entirety.

FIELD OF THE DISCLOSURE

The present disclosure is related to methods of treating pregnant mammals to reduce, prevent, or delay preterm birth.

BACKGROUND

In the United States, preterm birth remains the leading cause of neonatal morbidity and mortality, and worldwide complications from preterm birth result in 3.1 million neonatal deaths annually. Despite the short and long term health consequences of preterm birth and the sizeable health care costs, research efforts thus far have resulted in marginal improvements on the preterm birth rate. This lack of progress reflects a poor understanding of the mechanisms and molecules that mediate preterm birth. Spontaneous preterm birth is considered a complex syndrome with various etiologies ranging from decidual hemorrhage to uterine distension, but the most frequently cited etiology appears related to a pro-inflammatory process from pregnancy related reproductive tissues.

What is needed are compositions and methods for the reduction, prevention or delay of preterm birth.

BRIEF SUMMARY

In one aspect, a method of treating a pregnant female subject comprises administering to the pregnant female subject an effective amount of a Granulocyte Macrophage-Colony Stimulating Factor (GM-CSF) inhibitor, wherein the effective amount of the GM-CSF inhibitor is effective to reduce, prevent or delay preterm birth.

Figure 1:
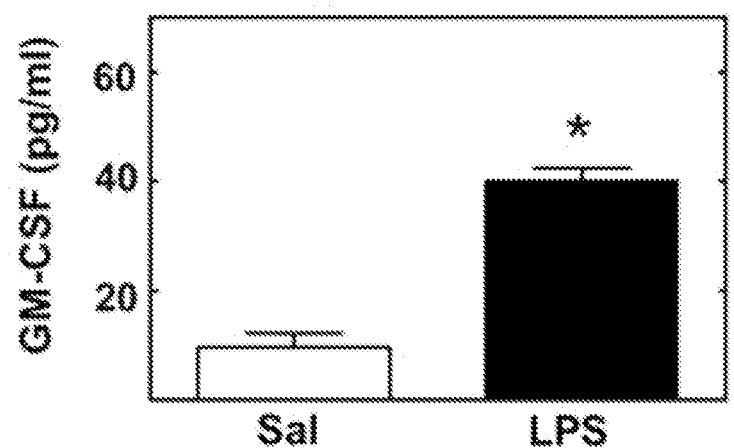
FIG. 1 is a bar graph representing the mean and standard error of the mean (SEM) demonstrating the effect of 25 µg/ml of lipopolysaccharide (LPS) for 24 hours increased the concentration of GM-CSF from ectocervical cells ($*p<0.001$).
Figure 2:
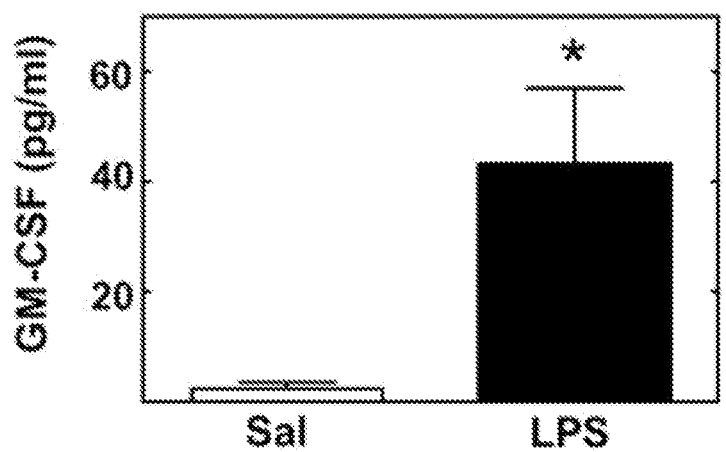
FIG. 2 is a bar graph representing the mean and standard error of the mean (SEM) demonstrating the effect of 25 µg/ml of lipopolysaccharide (LPS) for 24 hours increased the concentration of GM-CSF from endocervical cells ($*p<0.0005$).
Figure 3:
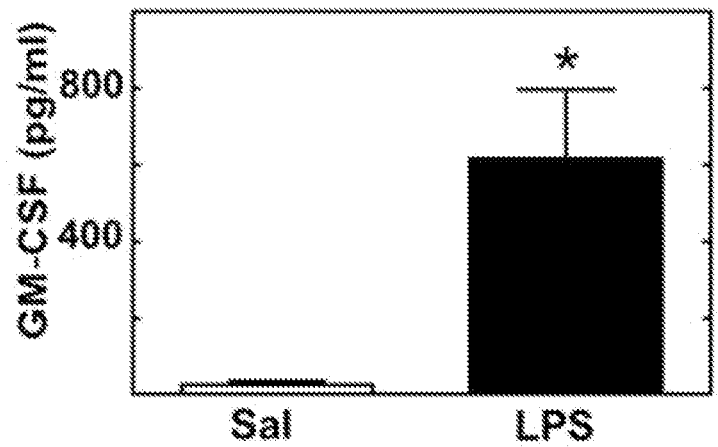
FIG. 3 is a bar graph representing the mean and standard error of the mean (SEM) demonstrating the effect of 25 µg/ml of lipopolysaccharide (LPS) for 24 hours increased the concentration of GM-CSF from AF-MSCs ($*p<0.001$) compared to saline (Sal) controls by t test.
Figure 4:
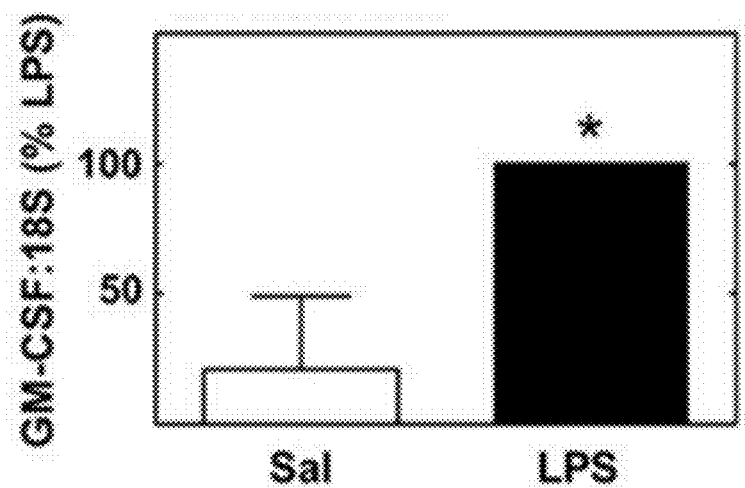
FIG. 4 shows that LPS also increased the expression of GM-CSF from ectocervical cells ($*p<0.0005$) compared to Sal controls using qPCR by t test (N=3-4 per treatment group.
Figure 5:
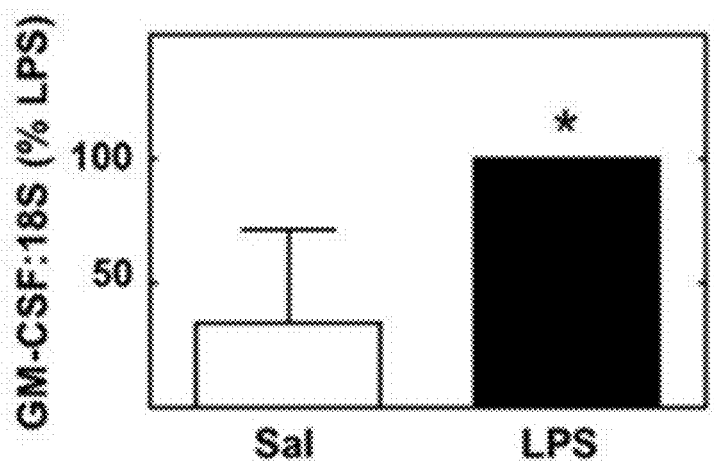
FIG. 5 shows that LPS also increased the expression of GM-CSF from endocervical cells ($*p<0.01$) compared to Sal controls using qPCR by t test (N=3-4 per treatment group.
Figure 6:
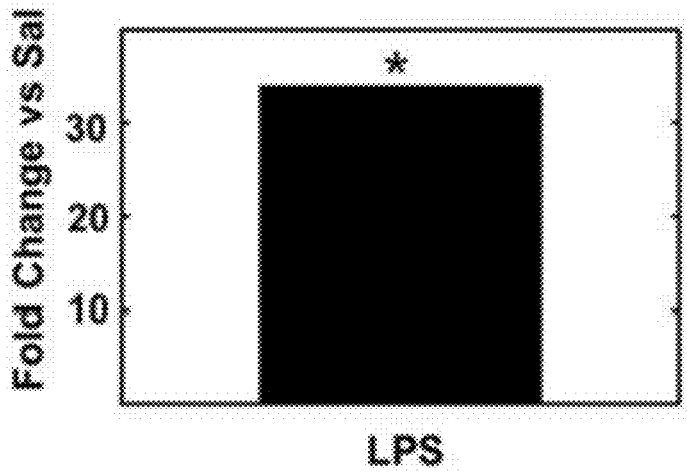
FIG. 6 shows that LPS also increased the expression of GM-CSF from AF-MSCs ($*p<0.0001$) compared to Sal controls using qPCR by t test (N=3-4 per treatment group.

The above-described and other features will be appreciated and understood by those skilled in the art from the following detailed description, drawings, and appended claims.

DETAILED DESCRIPTION

Macrophages are innate immune cells that contribute to preterm labor. Macrophages play a role in the rupture of fetal membranes, as they have been shown to produce matrix metallopeptidases 9 (MMP-9), an enzyme increased in fetal membranes in preterm labor and preterm premature rupture of membranes (PPROM). Additionally, macrophages produce vasoactive molecules (NO and prostaglandins) and pro-inflammatory cytokines which lead to edema and the release of MMPs by the fetal membranes leading to PPROM and prepartum changes in the reproductive tract. Similarly in rodents, the number of macrophages in the cervix peaks prior to birth, a period where the cervix softens and ripens and progesterone in the circulation is at or near peak concentrations. This increased presence or activity of macrophages leads to the increase in leukocyte collagenases which are thought to promote prepartum extracellular matrix remodeling during the transition from a soft to ripe cervix. Therefore, based on the increased presence and activity of macrophages prior to birth during cervical ripening, macrophages may play an essential role in preterm birth.

Granulocyte-macrophage colony-stimulating factor (GM-CSF), a monomeric glycoprotein, may also be involved in the parturition process by stimulating stem cells to produce monocytes and promoting their maturation into macrophages in the tissue. In pathophysiologic circumstances, GM-CSF is secreted during a pro-inflammatory response by immune cells, endothelial cells, and fibroblasts. Mature tissue-resident macrophages also produce GM-CSF to amplify the local inflammatory process, promote the additional recruitment of immune cells and mature tissue-resident macrophages, and stimulate the maturation of precursor cells.

Prior data has shown GM-CSF is linked with preterm birth. For example, serum GM-CSF concentrations elevated in women during the first trimester are at increased risk for preterm delivery. GM-CSF concentrations also are increased in vaginal swabs obtained from patients with a short cervix, a risk factor for spontaneous preterm birth. Similarly, in an inflammation-induced mouse model for preterm birth, serum GM-CSF concentrations increase within six hours of treatment. Together, these studies suggest increased prepartum concentrations of GM-CSF are associated with spontaneous preterm birth.

Thus, to determine whether GM-CSF has a role in the mechanism of inflammation initiated preterm labor and preterm birth, a series of experiments using multiple different reproductive tissue-derived cell lines were used to determine potential cites of GM-CSF production. To determine if GM-CSF plays a direct mechanistic role in controlling preterm birth, an inflammatory mouse model was used to test if a therapeutic blockade of GM-CSF inhibits critical features of cervical remodeling and prevents preterm birth.

In an aspect, a method of treating a pregnant female subject comprises administering to the pregnant female subject an effective amount of a Granulocyte Macrophage-Colony Stimulating Factor (GM-CSF) inhibitor, wherein the effective amount of the GM-CSF inhibitor is effective to reduce, prevent or delay preterm birth. In an aspect, preterm birth is spontaneous preterm birth.

As used herein, a "subject" is a female member of the class mammalia, including humans, domestic and farm animals, and zoo, sports or pet animals, such as mouse, rabbit, pig, sheep, goat, cattle, horse (e.g., race horse), and higher primates. In preferred embodiments, the subject is a human female.

As used herein, for pregnant human females, the term "preterm birth" is meant a birth that occurs before 37 weeks of gestation, e.g., between 20 to 37 weeks of gestation (e.g., 20 weeks to 26 weeks, 20 weeks to 30 weeks, 20 weeks to 36 weeks, or 34 weeks to 37 weeks of gestation).

In an aspect, pregnant human female presents to labor and delivery with symptoms of preterm birth. Symptoms of preterm birth include vaginal discharge, vaginal bleeding, pressure in the pelvis or lower belly, constant dull backache, belly cramps with or without diarrhea, painful or frequent contractions, and preterm breakage of membranes.

In an aspect, the pregnant female human subject is at risk of preterm birth. By the term "at risk of preterm birth" is meant a subject that has an increased risk of having a preterm birth as compared to a control population (e.g., a group of subjects of substantially the same age and/or gestational stage, optionally a group of subjects that have never had a preterm birth (e.g., a group of subjects that have never had a preterm birth and/or have had at least one term birth), or a group of subjects that are pregnant and the pregnancy results in a term birth).

In an aspect, the pregnant human female subject at risk of preterm birth has a short cervical length, an infection, a placental anomaly, have had a prior cesarean delivery, has or had uterine fibroids, a connective tissue disorder, is pregnant from in vitro fertilization, diabetes, blood clotting problems, high blood pressure, vaginal bleeding, a personal history of preterm birth, a family history of preterm birth, a previous pregnancy with 18 months of the current pregnancy, a current multi-fetal pregnancy, a uterine abnormality, a cervical abnormality, is overweight before or during pregnancy, is underweight before or during pregnancy, or is carrying a fetus with known birth defects.

Exemplary connective disorders include like Ehlers-Danlos syndromes (also called EDS) and vascular Ehlers-Danlos syndrome (also called vEDS).

Exemplary infections include urinary tract infections, sexually transmitted infections, and vaginal infections.

please delete-very unlikely we would treat a patient alone based on race. In yet another aspect, the pregnant human female subject at risk of preterm birth is a human woman under the age of 20 or over the age of 35.

In a further aspect, the pregnant human female subject at risk of preterm birth is a human woman engaging in smoking, engaging in drinking alcohol, using illegal drugs, with limited or no healthcare during pregnancy, subject to stress, subject to long working hours with long periods of standing, or exposed to environmental pollutants. Exemplary environmental pollutants include air pollution, lead, radiation, secondhand smoke, and the like.

In another aspect, the method comprises checking the female subject for signs of preterm labor. Exemplary methods of checking the female subject for signs of preterm labor include a cervical exam, a transvaginal ultrasound exam, testing for amniotic fluid, or testing for fetal fibronectin.

The methods may also comprise additional treatments such as treating with, administering tocolytic medicines, administering corticosteroids, performing cervical cerclage, and administering antibiotics. Tocolytic drugs are drugs used to delay delivery such as magnesium sulfate, beta-mimetics such as terbutaline, calcium channel blockers such as nifedipine and NSAIDs such as indomethacin.

Preterm birth can also be a problem for farm animals such as cattle, horses, sheep, and others. In addition, zoo animals such as non-human primates, red pandas, giant pandas, lions, hippos, elephants, and others.

Several GM-CSF inhibitors such as anti-GM-CSF antibodies are known in the art.

Mavrilimumab is a human IgG4 monoclonal antibody against GM-CSF receptor a which is in clinical trials for the treatment of rheumatoid arthritis. Mavrilimumab can be injected in doses of 10, 30, 50, 100 or 150 mg biweekly, for example.

Mavrilimumab (CAS No. 1085337-57-0) is described, for example, in U.S. Pat. Nos. 8,263,075 and 8,506,960. US20140335081 describes the use of mavrilimumab to treat rhuematoid arthritis. Mavrilimumab, as used herein, encompasses the mavrilimumab antibody comprising a heavy chain of SEQ ID NO: 1 and a light chain of SEQ ID NO: 2.

```
                                                    SEQ ID NO: 1
QVQLVQSGAEVKKPGASVKVSCKVSGYTLTELSIHWVRQAPGKGLEWMGG

FDPEENEIVYAQRFQGRVTMTEDTSTDTAYMELSSLRSEDTAVYYCAIVG

SFSPLTLGLWGQGTMVTVSSASTKGPSVFPLAPCSRSTSESTAALGCLVK

DYFPEPVTVSWNSGALTSGVHTFPAVLQSSGLYSLSSWTVPSSSLGTKTY

TCNVDHKPSNTKVDKRVESKYGPPCPSCPAPEFLGGPSVFLFPPKPKDTL

MISRTPEVTCVWDVSQEDPEVQFNWYVDGVEVHNAKTKPREEQFNSTYRW

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

SEQ ID NO: 2
QSVLTQPPSVSGAPGQRVTISCTGSGSNIGAPYDVSWYQQLPGTAPKLLI

YHNNKRPSGVDRFSGSKSGTSASLAITGLQAEDEADYYCATVEAGLSGSV

FGGGTKLTVLGQPKchainAAPSVTLFPPSSEELQANKATLVCLISDFYP

GAVTVAWKADSSPVKAGVETTTPSKQSNNKYAASSYLSLTPEQWKSHRSY

SCQVTHEGSTVEKTVAPTECS
```

Otilimab (CAS No. 1638332-55-4) (MOR103) is a fully human monoclonal antibody against GM-CSF which is in clinical trials for the treatment of rheumatoid arthritis and multiple sclerosis. MOR103 can be injected in doses of 0.3, 0.5, 1.0, 1.5 and 2.0 mg/kg weekly. U.S. Pat. No. 7,867,495, incorporated by reference herein, describes MOR103. MOR103 has a heavy chain of SEQ ID NO: 3 and a light chain of SEQ ID NO: 4.

```
                                                    SEQ ID NO: 3
QVQLVESGGGLVQPGGSLRLSCAASGFTFSSYWMNWVRQAPGKGLEWVSG

IENKYAGGATYYAASVKGRFTISRDNSKNTLYLQMNSLRAEDTAVYYCAR

GFGTDFWGQGTLVTVSSASTKGPSVFPLAPSSKSTSGGTAALGCLVKDYF

PEPVTVSWNSGALTSGVHTFPAVLQSSGLYSLSSWTVPSSSLGTQTYICN

VNHKPSNTKVDKRVEPKSCDKTHTCPPCPAPELLGGPSVFLFPPKPKDTL

MISRTPEVTCVWDVSHEDPEVKFNWYVDGVEVHNAKTKPREEQYNSTYRW

SVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGS

FFLYSKLTVDKSRWQQG NVFSCSVMHEALHNHYTQKSLSLSPGK

SEQ ID NO: 4
DIELTQPPSVSVAPGQTARISCSGDSIGKKYAYWYQQKPGQAPVLVIYKK

RPSGIPERGSGS NSGNTATLTISGTQAEDEADYYCSAWGDKGMVFGGGT

KLTVLGQ
```

TJM2 (TJ003234) is a humanized immunoglobulin G1 (IgG1) targeting granulocyte-macrophage colony-stimulating factor (GM-CSF). TJM2 is being developed by I-Mab Biopharma for the treatment of autoimmune and inflammatory diseases such as rheumatoid arthritis.

Lenzilumab (CAS No. 1229575-09-0) (KB003) is a humanized monoclonal antibody targeting GM-CSF. Lenzilumab has been shown to improve the effectiveness of CAR-T. Exemplary doses of lenzilumab are 10, 50 and 100 mg/kg. Lenzilumab has a heavy chain of SEQ ID NO: 5 and a light chain of SEQ ID NO: 6.

```
                                                    SEQ ID NO: 5
QVQLVQSGAEVKKPGASVKVSCKASGYSFTNYYIHWVRQAPGQRLEWMGW

INAGNGNTKYSQKFQGRVTITRDTSASTAYMELSSLRSEDTAVYYCVRRQ

RFPYYFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

SEQ ID NO: 6
EIVLTQSPATLSVSPGERATLSCRASQSVGTNVAWYQQKPGQAPRVLIYS

TSSRATGITDRFSGSGSGTDFTLTISRLEPEDFAVYYCQQFNKSPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Namilumab (CAS No. 1206681-39-1) is a human monoclonal antibody against GM-CSF in clinical trials for rheumatoid arthritis and psoriasis. Namilumab can be injected in doses of 40, 100, 150, 160 or 300 mg biweekly. Namilumab is described in U.S. Pat. No. 8,017,748. Namilumab has a heavy chain of SEQ ID NO: 7 and a light chain of SEQ ID NO: 8.

(heavy chain peptide sequence-Namilumab)
SEQ ID NO: 7
QVQLVQSGAEVKKPGASVKVSCKAFGYPFTDYLLHWVRQAPGQGLEWVGW

LNPYSGDTNYAQKFQGRVTMTRDTSISTAYMELSRLRSDDTAVYYCTRTT

LISVYFDYWGQGTMVTVSSASTKGPSVFPLAPSSKSTSGGTAALGCLVKD

YFPEPVTVSWNSGALTSGVHTFPAVLQSSGLYSLSSWTVPSSSLGTQTYI

CNVHKPSNTKVDKKVEPKSCDKTHTCPPCPAPELLGGPSVFLFPPKPKDT

LMISRTPEVTCVWDVSHEDPEVKFNWYVDGVEVHNAKTKPREEQYNSTYR

WSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK (light chain peptide sequence-Namilumab)
SEQ ID NO: 8
DIQMTQSPSSVSASVGDRVTIACRASQNIRNILNWYQQRPGKAPQLLIYA

ASNLQSGVPSRFSGSGSGTDFTLTINSLQPEDFATYYCQQSYSMPRTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Gimsilumab (CAS No. 1648796-29-5) (MORAb-022) is a fully human monoclonal antibody being evaluated for its potential in the treatment of multiple inflammatory diseases and cancer. Gimsilumab has a heavy chain of SEQ ID NO: 9 and a light chain of SEQ ID NO: 10.

SEQ ID NO: 9
EVQLVESGGGLVQPGGSLRLSCAASGFTFSRHWMHWLRQVPGKGPVWVSR

INGAGTSITYADSVRGRFTISRDNANNTLFLQMNSLRADDTALYFCARAN

SVWFRGLFDYWGQGTPVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVVHEALHNHYTQKSLSLSPG

K

SEQ ID NO: 10
EIVLTQSPVTLSVSPGERVTLSCRASQSVSTNLAWYQQKLGQGPRLLIYG

ASTRATDIPARFSGSGSETEFTLTISSLQSEDFAVYYCQQYDKWPDTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Additional anti-GM-CSF antibodies include PD-0360324.

Peptides that inhibit GM-CSF by inhibiting the interaction of GM-CSF and its receptor include SEQ ID NO: 11 (CGKASATKGKGEATGGC), SEQ ID NO: 12 (CGTAE-GKGGKGTASAKGGC), SEQ ID NO: 13 (QPWEHVNAI-QERRLLNLSR), SEQ ID NO: 14 (KDFLL-VIPFDCWEPVQE), SEQ ID NO: 15 (FQYQLDVHRKN); and SEQ ID NO: 16 (ADVRILN) as described in U.S. Pat. No. 9,453,050. In an aspect, the peptide comprises any one of SEQ ID NOs. 11-16, or a variant with 95% or more homology to any one of SEQ ID NOs. 11-16.

In another aspect, the GM-CSF inhibitor comprises an inhibitory nucleic acid that reduces the expression of GM-CSF or GM-CSF receptor. For example, small interfering RNAs (siRNAs) and antisense RNAs can be used. Useful inhibitory nucleic acids include those that reduce the expression of GM-CSF or its receptor by at least 10%, 20%, 30%, 40%, 50%, 60%, 70%, 80%, 90%, 95% or 99% in a cell or tissue compared to a cell or tissue that has not been exposed to the inhibitory nucleic acid.

RNAi is a process whereby double-stranded RNA (dsRNA, also referred to herein as siRNAs or ds siRNAs, for double-stranded small interfering RNAs) induces the sequence-specific degradation of homologous mRNA in animals and plant cells. In mammalian cells, RNAi can be triggered by 21-nucleotide (nt) duplexes of small interfering RNA (sRNA), or by micro-RNAs (miRNA), functional small-hairpin RNA (shRNA), or other dsRNAs which are expressed in vivo using DNA templates with RNA polymerase III promoters.

The nucleic acid molecules or constructs can include dsRNA molecules comprising 16-30, e.g., 16, 17, 18, 19, 20, 21, 22, 23, 24, 25, 26, 27, 28, 29, or nucleotides in each strand, wherein one of the strands is substantially identical, e.g., at least 80% (or more, e.g., 85%, 90%, 95%, 99% or 100%) identical, e.g., having 3, 2, 1, or 0 mismatched nucleotide(s), to a target region in the mRNA, and the other strand is complementary to the first strand. The dsRNA molecules can be chemically synthesized, or can transcribed in vitro from a DNA template, or in vivo from, e.g., shRNA. The dsRNA molecules can be designed using any method known in the art; a number of algorithms are known, and are commercially available.

An "antisense" nucleic acid can include a nucleotide sequence that is complementary to a "sense" nucleic acid encoding a protein, e.g., complementary to the coding strand of a double-stranded cDNA molecule or complementary to an integrin ligand mRNA sequence. The antisense nucleic acid can be complementary to an entire coding strand of a target sequence, e.g., an mRNA, or to only a portion thereof. According to some embodiments, the antisense nucleic acid molecule is antisense to a "noncoding region" of the coding strand of a nucleotide sequence (e.g., the 5' and 3' untranslated regions). For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

The terms "effective amount," "therapeutically effective amount and "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising the compound as disclosed herein required to provide a clinically significant decrease in acute urticaria.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The term "acceptable" as used herein, with respect to a formulation, composition or ingredient, means having no persistent detrimental effect on the general health of the subject being treated.

The invention is further illustrated by the following non-limiting examples.

EXAMPLES

Methods

Cervical Cell Culture and Preparation:

Immortalized HPV 16/E6E7 ectocervical (ATCC CRL-2614) and endocervical (ATCC CRL-2615) cells (American Type Culture Collection, Manassas, Va.) were maintained in keratinocyte serum-free medium (GIBCO BRL Life Technologies, Gaithersburg, Md.) supplemented with 50 µg/ml bovine pituitary extract (BPE), 0.1 ng/ml epidermal growth factor (EGF), 100 U/ml penicillin, and 100 µg/ml of streptomycin (Life Technologies, Grand Island, N.Y.) at 37° C. in a 5% $CO_2$ humidified incubator.

Amniotic Fluid Mesenchymal Stem Cell Culture and Preparation:

Human amniotic fluid mesenchymal stem cells (AF-MSCs) were studied to determine if cells within the amniotic cavity have the potential to produce GM-CSF. Briefly, AF-MSCs were obtained from patients undergoing amniocentesis at Hartford Hospital (Hartford Hospital IRB #FINC003364HU). The discarded sample (~5 mL) was collected and AF-MSCs were manually isolated by the published starter cell method.

AF-MSCs were maintained in AF Media, which consists of MEM alpha medium (Life Technologies, Grand Island, N.Y.) containing 18% Chang Medium® B (Irvine Scientific, Santa Ma, Calif.), 2% Chang Medium® C (Irvine Scientific, Santa Ana, Calif.), 20% Fetal Bovine Serum (FBS) (Atlanta Biologicals, Lawrenceville, Ga.), 2 mM L-Glutamine (Life Technologies, Grand Island, N.Y.), 100 U/ml penicillin, and 100 µg/ml of streptomycin (Life Technologies, Grand Island, N.Y.) at 37° C. in a 5% $CO_2$ humidified incubator. AF-MSC's utilized were less than passage ten.

Detection of Soluble Immunobiological Mediators:

Ectocervical and endocervical cells were plated at a concentration of $9.6 \times 10^4$ cells per well ($1.07 \times 10^4$ cells/cm$^2$) on six well plates for 24 hours in keratinocyte serum-free medium containing BPE, EGF, penicillin, and streptomycin. Cells were then treated with keratinocyte serum-free media containing only penicillin and streptomycin for an additional 24 hours prior to LPS treatment. AF-MSCs were plated at a concentration $1 \times 10^4$ cells/cm$^2$ in AF media for 24 hours. All three cell lines were treated with 25 µg/ml of lipopolysaccharide strain *Escherichia Coli* 055:B5 (LPS) (Sigma Chemical Company, St. Louis, Mo.) (N=3-4 per treatment group in all three cell lines) for 24 hours. Media was collected and assessed for GM-CSF using an ELISA (R&D Systems, Minneapolis Minn.) and analyzed according to the manufactures protocol. RNA was collected for quantitative real time PCR (qRT-PCR) for expression of GM-CSF.

Mouse Model of Intrauterine Inflammation:

All procedures were performed with Institutional Animal Care and Use Committee approval from the University of Connecticut School of Medicine. As previously reported, this model mimics the clinical scenario of an inflammatory response in the uterus leading to a spontaneous preterm birth and does not result in maternal mortality. CD-1 timed pregnant mice (Charles River Laboratories, Wilmington, Mass.) received an intrauterine injections of LPS (*Escherichia coli*, 055: B5, Sigma Chemical Co, St Louis, Mo.) at a dose of 250 µg in 100 nt of phosphate-buffered saline (PBS) on embryonic day 17 (E17). The treatment day of E17 was chosen to mimic the typical clinical presentation of intrauterine inflammation associated with presentation of cervix ripening and preterm labor. The survival surgeries were performed by placing the pregnant mouse under a mask maintaining a continuous flow of isoflurane to obtain adequate deep anesthesia. A mini-laparotomy was then performed in the lower abdomen; LPS or saline was infused into the right uterine horn between the first and second gestational sacs (just cephalad from the cervix). Peritoneal closure was performed with sutures and the incision closed with staples. Mice were monitored until either the birth of the first pup or up to six hours, after which the dams were euthanized with carbon dioxide. For these experiments, preterm birth was defined as delivering at least one mouse pup thru the cervix within six hours of the intrauterine injection. Each cervix and uterus was harvested and flash frozen with liquid nitrogen for messenger RNA (mRNA) expression. Samples were stored at −80° C. until processed for quantitative polymerase chain reaction (qPCR) analysis as described below. Sixteen animals received an intrauterine injection either LPS or saline.

A second series of experiments were performed to determine if systemic treatment with an antibody to GM-CSF would prevent preterm birth or impact cervical remodeling. Mice were treated as described above, and immediately after the intrauterine injection of LPS while still anesthetized, a 200 µg/100 µl retro-orbital injection was administered containing either an anti-mouse GM-CSF antibody (Bio X Cell, West Lebanon N.H., Catalog #BE0259) or a nonspecific isotype IgG control antibody (Bio X Cell, Catalog #BE0089). The particular IgG control antibody was chosen to match the isotype and species of the GM-CSF, thus to mimic any nonspecific xenogeneic reaction to treatment. Mice were again monitored until either the birth of the first pup or up to six hours, after which the dams were euthanized with carbon dioxide. The cervix was harvested, flash frozen with liquid nitrogen and shipped to Loma Linda University for histology and analyses (see below). In addition, the amniotic fluid and serum was collected to determine the concentration of GM-CSF by ELISA (BioLegend, San Diego Calif.) and analyzed according to the manufacture's protocol.

A power analysis was performed to determine if the GM-CSF antibody statistically decreases the rate of preterm birth compared to the isotype control antibody in mice receiving an intrauterine injection of LPS. We estimated the preterm birth rate within 6 hours would be 75% in mice receiving LPS and the control antibody, and 20% in mice receiving LPS and the GM-CSF antibody. Assuming an alpha of 0.05 and a power of 80%, we estimated we would need 12 animals per treatment group.

Cervix histology and analyses: Cervix were immersion fixed in fresh 4% paraformaldehyde, transferred the next day to 70% ethanol, paraffin-embedded, sectioned (6 µm), and stained with a picrosirius red to identify cross-linked collagen. Optical density (OD) of polarized light birefringence from picrosirius red stain reflects cross-linked collagen fibers in the extracellular matrix of the stroma. Other sections were stained to identify mature Mφs (F4/80 antibody 1:800 dilution, T-2006; Bachem, Torrance, Calif.) and counterstained with hematoxylin to visualize cell nuclei as previously described. Sections were imaged with an Aperio ScanScope® microscope and 8-16 photomicrographs (300× 417 µm) taken from each of two cross-sections of cervix for each mouse. Cell nuclei and Mφs in stroma were counted using NIH Image J with care taken to exclude blood vessels, lumen, epithelium, and other atypical structures. As before, Mφs were defined as brown stain within a cell boundary in proximity to a hematoxylin-stained cell nuclei. Collagen and Mφ numbers/area were normalized to total number of cells/area for each animal to adjust for heterogeneity of anatomy that occurs within and among sections, as well as individuals. All cervices analyzed from mice receiving LPS only or LPS and the GM-CSF control antibody delivered within six hours. Cervices analyzed from mice receiving LPS and the GM-CSF neutralizing antibody did not deliver within six hours.

Quantitative Polymerase Chain Reaction:

Total RNA was extracted from both the immortalized ectocervical and endocervical cells after 24 hours of LPS exposure and the mouse cervix and uterus using Qiagen RNeasy® Mini Kits according to product protocol. Complementary DNA (cDNA) was generated from 1 µg of RNA/sample using a cDNA reverse transcription kit (Bio-Rad Laboratories, Hercules, Calif.). To assess expression, quantitative polymerase chain reaction (qPCR) was performed using equivalent dilutions of each sample on a Bio-Rad CFX qPCR instrument (N=3-4 per treatment group). The CSF2 primers assays Hs00929873_ml and Mm01290062_ml conjugated to Taqman® MGB probes were utilized in this analysis (Applied Biosystems, Foster City, Calif.). The relative abundance of GM-CSF was divided by the relative abundance of 18S in each sample to generate a normalized abundance. All samples were analyzed in triplicate and each experiment or N was analyzed separately and divided by the values of LPS and multiplied by 100 in order to present the results as percent LPS.

For AF-MSCs, RNA was extracted using Qiagen RNeasy® Mini Kits according to product protocol. Complementary DNA (cDNA) was generated from 1 µg of RNA/sample using the Qiagen miScript® II RT Kit. To assess expression, quantitative polymerase chain reaction (qPCR) was performed using equivalent dilutions of each sample (N=4 per treatment group) using $RT^2$ Profiler PCR custom array plates in combination with $RT^2$ SYBR® Green Mastermixes on a Bio-Rad CFX qPCR instrument. The relative abundance of GM-CSF was determined using the $\Delta\Delta C_T$ method.

Lactate Dehydrogenase Cytotoxicity Assay:

The viability of AF-MSCs after treatment with 25 ug/ml of LPS was determined by measuring lactate dehydrogenase (LDH) leaking into the medium using the Pierce™ LDH Cytoxicity Assay (Thermo Scientific, Waltham, Mass.) (N=4 per treatment group). After collecting cell culture medium, the cells were lysed with reaction mixture containing substrate mix (lyophilizate) and assay buffer. Extracellular LDH in the media was quantified using a coupled enzymatic reaction in which LDH catalyzes the conversion of lactate to pyruvate via $NAD^+$ reduction to NADH. Diaphorase then uses NADH to reduce a tetrazolium salt (INT) to a red formazan product that can be measured at 490 nm. The level of formazan formation is directly proportional to the amount of LDH released into the medium, which is indicative of cytotoxicity. We have previously published 25 ug/ml of LPS is not cytotoxic to ectocervical and endocervical cells and therefore the cytotoxicity assay was not performed on these cell lines.

Statistical Analysis:

Statistical analyses were performed comparing means or medians depending on whether the data were parametric (normally distributed $p > 0.05$ Levene's test followed by Student's t test or one-way ANOVA) or non-parametric (Mann-Whitney test or ANOVA on ranks). If significance was met for multiple comparisons, pair-wise comparison was then performed using Student-Newman-Keuls (SNK). Analysis was performed by running Graph Pad Prism software (GraphPad, San Diego, Calif.).

Example 1: LPS Activates Release and Upregulates GM-CSF in Cervical Epithelial Cells and AF-MSCs Treatment with LPS resulted in an increase in GM-CSF concentrations after 24 hours in ectocervical cells ($p < 0.0001$), endocervical cells ($p < 0.0005$), and AF-MSCs ($p < 0.01$) as measured by ELISA. Expression of GM-CSF by real time qPCR increased in ectocervical cells ($p < 0.0005$), endocervical cells ($p < 0.01$), and AF-MSC's ($p < 0.0001$) (FIGS. 1-6). Thus, LPS increases the concentration and gene expression of GM-CSF from cervical epithelial and AF-MSC's.

Example 2: Treatment with LPS Did not Increase LDH

While exposure to LPS leads to an increase in GM-CSF concentration, LPS had no effect on the concentration of LDH compared to controls in AF-MSCs after 24 hours (data not shown) using the LDH assay ($p = 0.61$). This finding is consistent with previous evidence that LPS does not induce cell death in ectocervical and endocervical cells.

Example 3: LPS Increases Expression of GM-CSF in the Mouse Cervix and Uterus

Figure 7:
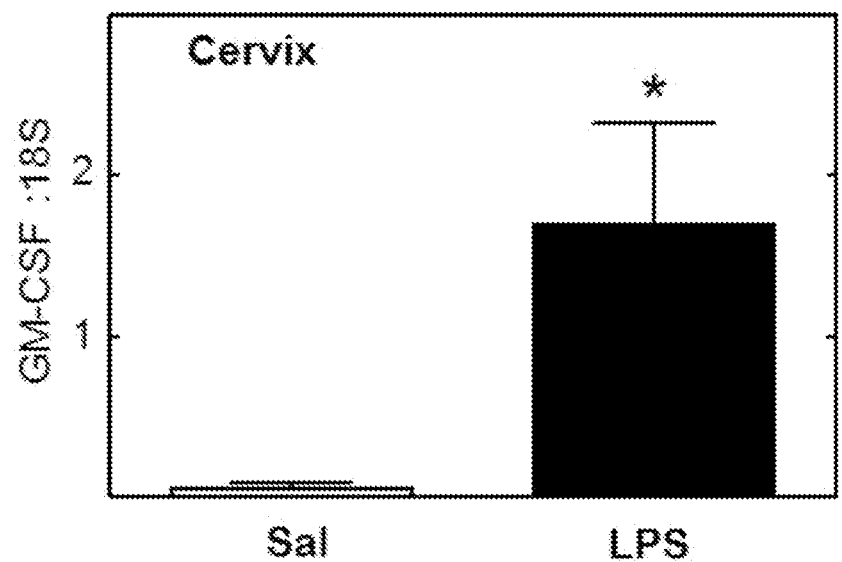
FIG. 7 is a bar graph depicting the mean and SEM demonstrating the effect of LPS on the expression of GM-CSF six hours after an intrauterine injection of 250 µg of lipopolysaccharide (LPS). LPS increased the expression of GM-CSF from the mouse cervix ($*p<0.005$) compared to mice receiving an intrauterine injection of Sal by t test.
Figure 8:
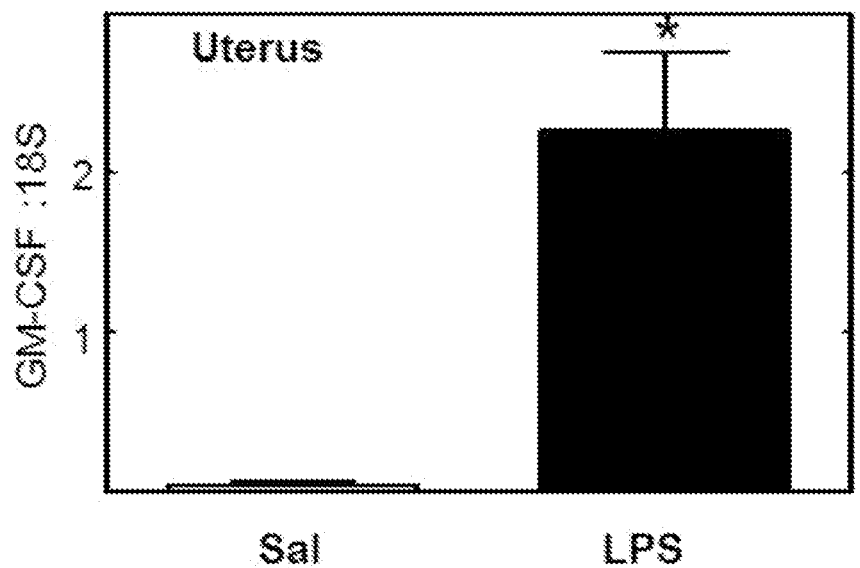
FIG. 8 is a bar graph depicting the mean and SEM demonstrating the effect of LPS on the expression of GM-CSF six hours after an intrauterine injection of 250 µg of lipopolysaccharide (LPS). LPS increased the expression of GM-CSF from the mouse uterus ($*p<0.0001$) compared to mice receiving an intrauterine injection of Sal by t test.

GM-CSF expression was increased in the cervix and uterus of mice treated with an intrauterine injection of LPS compared to control mice that received saline (p<0.005, FIGS. 7 and 8). Thus, LPS is a potent promotor of GM-CSF expression.

Figure 9:
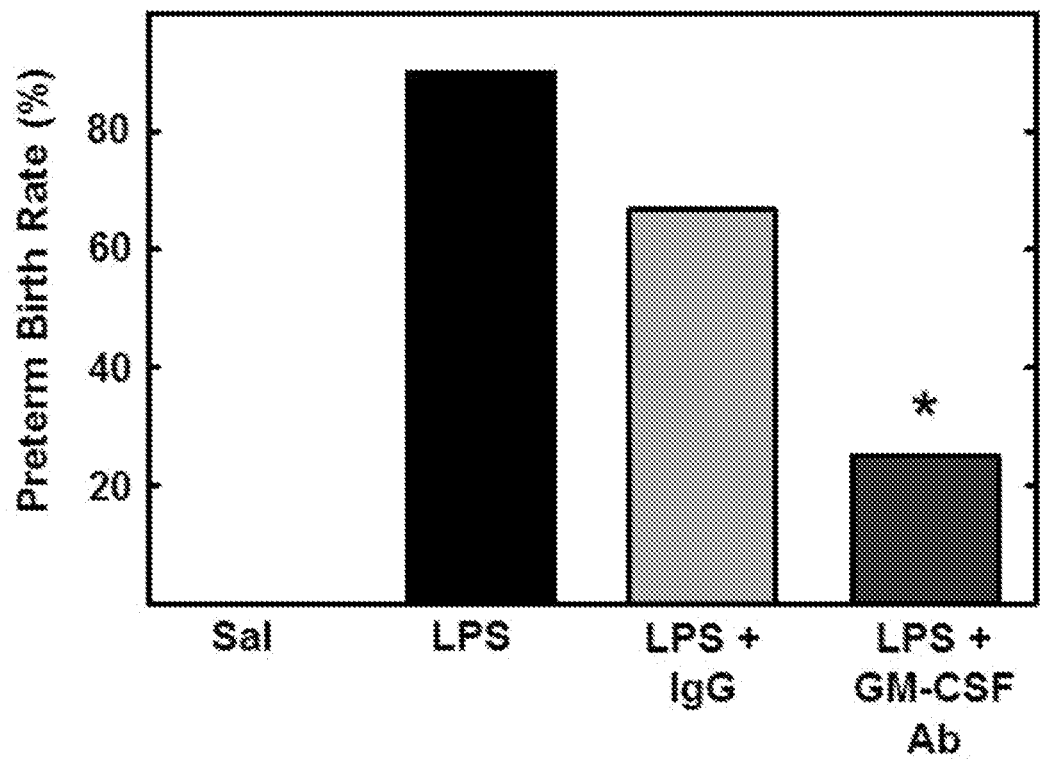
FIG. 9 shows mice treated with an intrauterine injection of saline (Sal) and lipopolysaccharide (LPS) had a preterm birth rate (process of delivering) within six hours of 0% and 87.5%, respectively. Mice treated with LPS and the isotype control antibody (LPS+IgG) had a preterm birth rate of 66.7% compared to a 25% preterm birth rate in mice receiving LPS and the anti-mouse GM-CSF antibody (LPS+GM-CSFab) ($*p<0.05$ chi square).

Example 4: GM-CSF Blockade Therapy Prevents LPS Induced Preterm Birth and Decreases the GM-CSF Concentration in the Serum and Amniotic Fluid Inflammation-induced preterm birth, defined as delivering a mouse pup thru the cervix within six hours, was reduced with GM-CSF antibody treatment. Within 6 hours of an intrauterine LPS injection, 87.5% (14 of 16) of mice where in the process of delivering at least one pup compared to 0 of 16 mice receiving an intrauterine injection of saline (FIG. 9). In mice administered both LPS and a control isotype IgG antibody, 66.67% (8 of 12) were in the process of delivering preterm within six hours. Of the 12 mice receiving LPS and the GM-CSF antibody, 75% (9 of 12) had not delivered within six hours, for a preterm birth rate of 25% (p<0.05, chi square).

Figure 10:
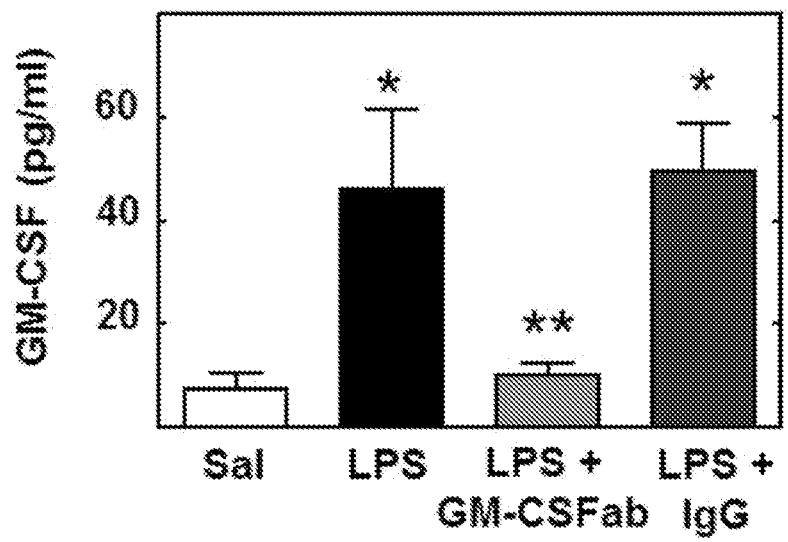
FIG. 10 is a bar graph depicting the mean and SEM demonstrating the concentration of GM-CSF in the serum of mice treated with saline (Sal), lipopolysaccharide (LPS), LPS and the GM-CSF antibody (LPS+GM-CSFAb), and LPS and the control antibody (LPS+IgG). The concentration of GM-CSF was increased with LPS and LPS+IgG compared to mice treated with Sal ($*p<0.0001$) in the serum but not in the amniotic fluid. Treatment with the GM-CSF antibody decreases the concentration of GM-CSF in the serum ($**p<0.001$) and amniotic fluid ($*p<0.01$), one-way ANOVA, student newman keuls (SNK).
Figure 11:
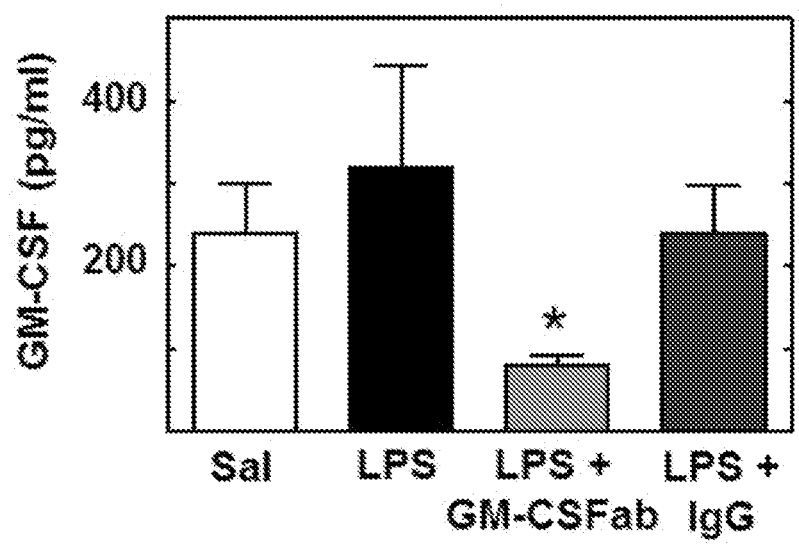
FIG. 11 is a bar graph depicting the mean and SEM demonstrating the concentration of GM-CSF in the amniotic fluid of mice treated with saline (Sal), lipopolysaccharide (LPS), LPS and the GM-CSF antibody (LPS+GM-CSFAb), and LPS and the control antibody (LPS+IgG). The concentration of GM-CSF was increased with LPS and LPS+IgG compared to mice treated with Sal ($*p<0.0001$) in the serum but not in the amniotic fluid. Treatment with the GM-CSF antibody decreases the concentration of GM-CSF in the serum ($**p<0.001$) and amniotic fluid ($*p<0.01$), one-way ANOVA, student newman keuls (SNK).

Treatment with the GM-CSF antibody also decreased the concentration of GM-CSF in the serum. In mice receiving LPS only or LPS along with the IgG control antibody, serum concentrations of GM-CSF were significantly increased compared to saline controls and LPS+GM-CSF antibody mice (p<0.001). Additionally, GM-CSF antibody treatment decreased the concentration of GM-CSF in the amniotic fluid compared to the three other groups (FIGS. 10 and 11). Thus, suppressing GM-CSF in serum was associated with a reduced incidence of preterm birth.

Example 5: GM-CSF Antibody Effects on Characteristics of Cervix Remodeling

Figure 12:
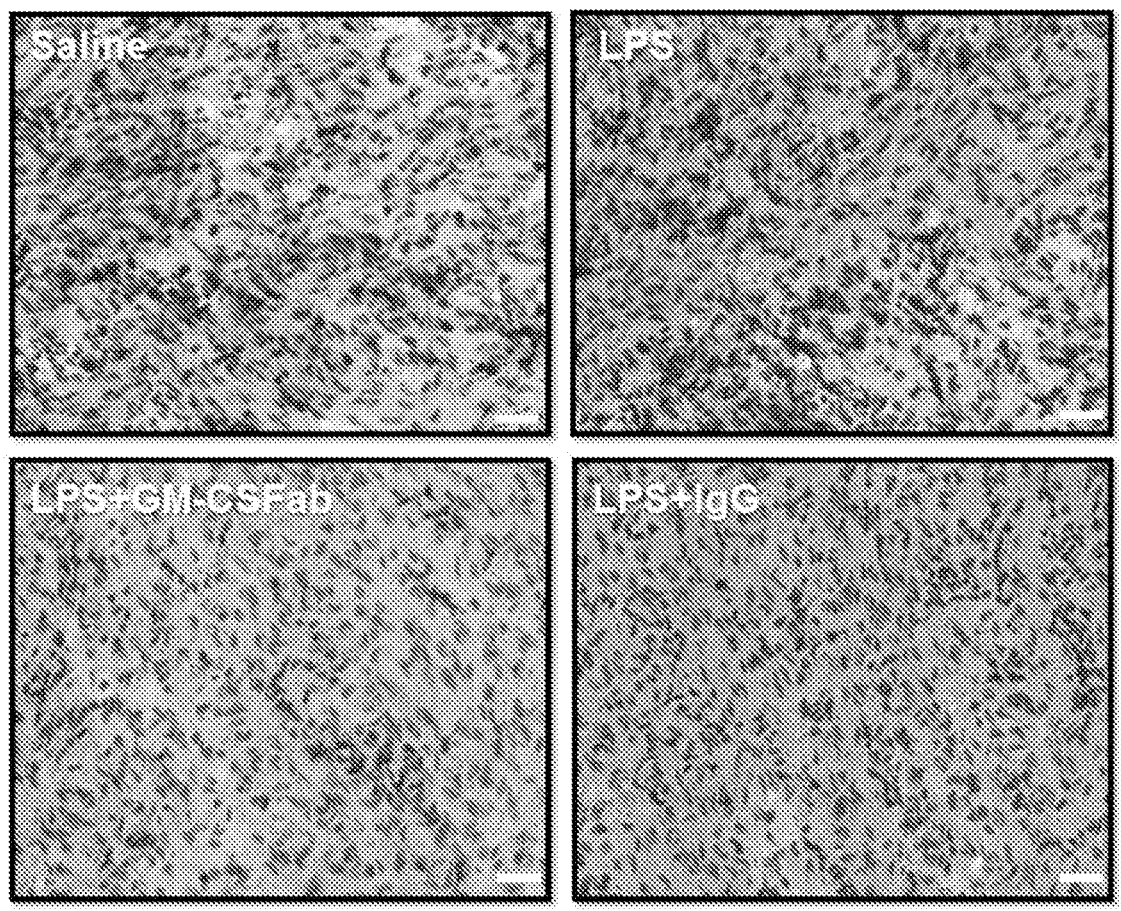
FIG. 12 shows photographs of cervix from day 17 pregnant mice injected with treatments six hours earlier. Left to right: Saline (Sal), lipopolysaccharide (LPS), LPS+ granulocyte macrophagecolony stimulating factor antibody (LPS+GM-CSFab), or LPS+ isotype control antibody (LPS+IgG) treated cervix (E17) stained by immunohistochemistry for macrophages (brown) with hematoxylin counterstain. Scale bar=25 µm.
Figure 13:
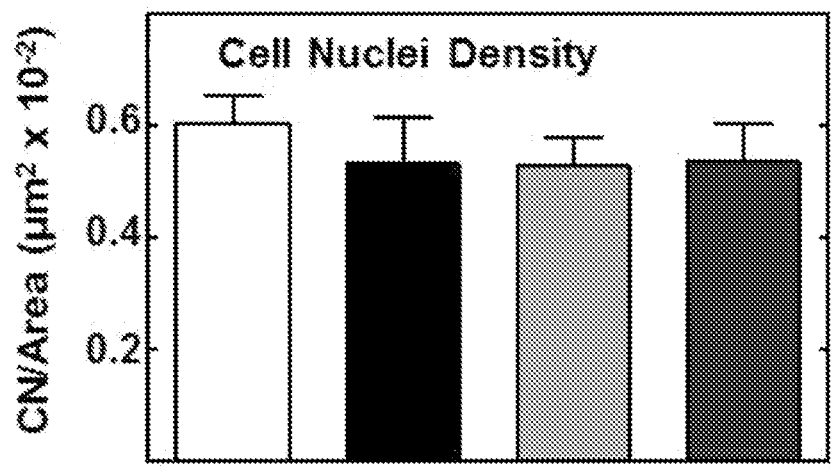
FIG. 13 shows the density of cell nuclei/area in the cervix stroma on day E17 of pregnancy treated with saline (Sal), lipopolysaccharide (LPS), LPS+granulocyte macrophage-colony stimulating factor antibody (LPS+GM-CSFab), or LPS+ isotype control antibody (LPS+IgG). Data are mean±SE. $*p<0.05$ vs Sal and LPS groups by ANOVA.
Figure 14:
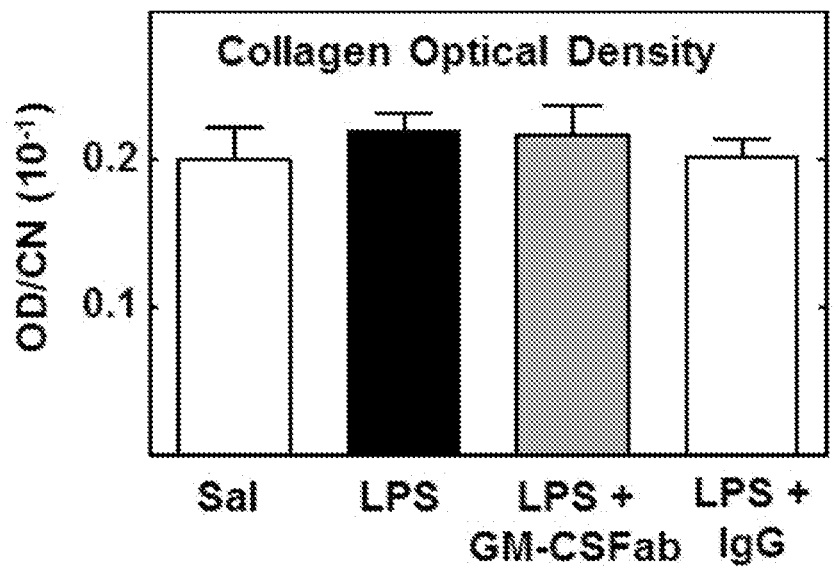
FIG. 14 shows the optical density of picrosirius red stained collagen in the cervix stroma on day E17 of pregnancy treated with saline (Sal), lipopolysaccharide (LPS), LPS+granulocyte macrophage-colony stimulating factor antibody (LPS+GM-CSFab), or LPS+ isotype control antibody (LPS+IgG). Data are mean±SE. *p<0.05 vs Sal and LPS groups by ANOVA.
Figure 15:
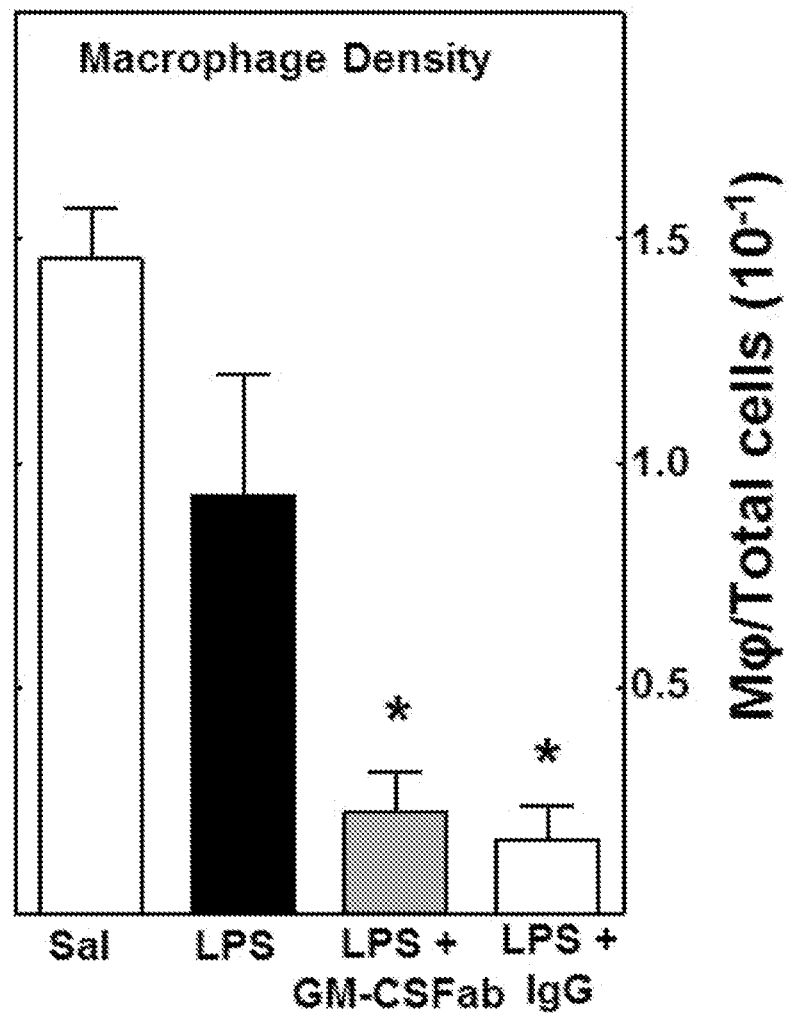
FIG. 15 shows the density of macrophage in the cervix stroma on day E17 of pregnancy treated with saline (Sal), lipopolysaccharide (LPS), LPS+granulocyte macrophage-colony stimulating factor antibody (LPS+GM-CSFab), or LPS+ isotype control antibody (LPS+IgG). Data are mean±SE. *p<0.05 vs Sal and LPS groups by ANOVA.

Images of the cervix stroma contained an abundance of purple-stained cell nuclei, a fraction of which were stained brown as an indication of the presence of mature macrophages. Abundance of macrophages, rather than morphology of cell nuclei or macrophages appeared to differ across sections with respect to treatments (FIG. 12). In response to treatment, neither the density of cell nuclei nor optical density of collagen birefringence in cervix stroma sections changed compared to mice in the saline group (FIGS. 13 and 14). However, macrophage density was reduced in cervix stroma in mice treated with the GM-CSF or IgG control antibody compared to those treated with either PBS or LPS. (FIG. 15).

Discussion: Using in vitro models, the results demonstrated GM-CSF is produced from ectocervical cells, endocervical cells, and AF-MSCs when challenged with LPS. GM-CSF is also upregulated in the cervix and uterus in a mouse model of preterm birth. Of critical importance, neutralization of systemic GM-CSF was associated with a decrease in the rate of inflammation-induced preterm birth, suggesting GM-CSF activity is a critical mediator in this animal model of inflammation-induced preterm parturition. Therefore, these findings raise the possibility systemic suppression of GM-CSF may be an approach to prevent preterm birth.

A pro-inflammatory immune response arising in reproductive tissue is believed to be a major component of preterm birth. Prior work on this topic has shown statins will decrease the preterm birth rate and the concentration of GM-CSF in the serum of mice treated with LPS. In addition, treatment with a broad spectrum chemokine inhibitor, which reduced serum concentration of several cytokines including GM-CSF, decreased the preterm birth rate in a mouse model of preterm birth. Although the function of GM-CSF is to increase the influx monocytes which differentiate into macrophages, the presence of macrophages in the cervix does not correlate with cervical function due to their heterogeneity. Activated macrophages will produce a number of cytokines and chemokines, including tumor necrosis factor (TNF), interleukin (IL)-1, IL-6, IL-8, and IL-12. Activated macrophages will also activate complement, and an increase in complement levels have been shown to mediate preterm birth. Thus, GM-CSF may decrease the number of activated differentiated macrophages in the cervix, resulting in a decrease in cytokines and complement thus decreasing preterm birth.

Treatment with the GM-CSF blocking antibody reduces the number of macrophages in the cervix within six hours after LPS to the same extent as the control isotype antibody. Although the effects of an inflammatory challenge on tissue resident immune cells has received little attention, this finding raises the possibility that reduced macrophage density in the cervix and perhaps other tissues may be in response to a xenogenic immune challenge. Nevertheless, the phenotype of macrophages and their local activity within six hours of LPS treatment and leading up to labor is likely different between mice receiving the blocking GM-CSF versus isotype control antibody, as mice receiving the GM-CSF antibody are less likely to deliver preterm. This focus on macrophage density and activity seems warranted as the neutralization of GM-CSF did not affect the cell nuclei density or extracellular cross-linked collagen structure in the peripartum cervix. This lack of GM-CSF effect was not expected, given that these endpoints of cervical remodeling (cellular hypertrophy, edema, and biomechanical compliance) are at or near plateau in a ripened cervix on day E17. Therefore, the mechanism by which the GM-CSF antibody prevents preterm birth is likely due to its ability to suppress macrophage activity and signaling rather than decreasing the number and density of macrophages in the cervix.

Of further interest is the counter-intuitive finding that macrophages in the cervix did not increase in mice receiving LPS alone despite preterm birth. This result is consistent with a previous study and may reflect the complexity of mature macrophage functions, i.e., inflammatory or regulatory, that are guided by local signals. These activities reflect macrophage phenotypes that would not be differentiated by staining for the F4/80 epitopes which reflects a role in phagocyte-related matrix interactions. Moreover, the time course of a changed census of residency by macrophages in the cervix may be overshadowed by effects of LPS to act directly upon toll like receptors on cervical stromal cells within the six hour period leading up to preterm birth. Although assessment of macrophage phenotypes and activities were beyond the scope in these studies, these findings raise the possibility that inflammation-induced ripening and preterm birth may accelerate pro-inflammatory processes in ways that differ from those at term parturition.

The use of immunomodulators have been widely used to treat a host of medical conditions ranging from cancers to autoimmune disorders, and specifically a monoclonal antibody to GM-CSF has been used to treat a variety of diseases including pediatric neuroblastomas, respiratory diseases, autoimmune disorders, and GI conditions. However, to our knowledge this is the first use of a GM-CSF antibody to prevent preterm birth. As the etiology of preterm birth and cervical remodeling is initiated by an upregulation of pro-inflammatory processes, and due to the increase in GM-CSF from multiple sites in the genital tract, our results were expected. Although counterintuitive, LPS did not alter the concentration of GM-CSF in the amniotic fluid, raising the possibility inflammation induced preterm birth is not acting thru a mechanism in the amniotic fluid. However, these results increase our understanding of the molecular pathways leading to preterm birth and may open up a new area of treatment modalities to decrease preterm birth and improve neonatal outcomes.

In summary, our results show the inhibition of GM-CSF during a pro-inflammatory immune response in the reproductive tract will prevent preterm birth. Our results also showed treatment with the GM-CSF antibody decreases the concentration of GM-CSF in the serum but does not alter the number of macrophages in the cervix, suggesting the GM-CSF antibody may be impacting macrophage function and activity. Further research is needed to determine if an antibody to GM-CSF could be utilized as a therapeutic agent to prevent spontaneous preterm birth.

In additional studies, Pregnant CD-1 mice on embryonic day 17 received an intrauterine injection of 10 μg of GM-CSF or vehicle control into each uterine horn. After 24 hours, mice were euthanized and assessed for vaginal pooling and arborized crystals or ferning. Uterine tissue was harvested and assessed for mRNA expression of matrix metallopeptidase (MMP) 9, extracellular MMP inducer (Emmprin), tissue inhibitor of metalloproteinase (TIMP) 2, tumor necrosis factor alpha (TNFα), and interleukin-6 (IL-6). Amniotic fluid was also collected and assessed for the concentration of GM-CSF using an ELISA.

75% of mice treated with GM-CSF exhibited either vaginal pooling or ferning, consistent with premature rupture of membranes (PPROM), while control mice did not exhibit any signs of PPROM. None of the mice treated with GM-CSF or vehicle control delivered within 24 hours. Mice treated with GM-CSF had increased uterine expression of MMP9 ($p<0.0005$), Emmprin ($p<0.0001$), and TIMP2 ($p<0.0001$). Additionally, GM-CSF also increased the expression of the pro-inflammatory cytokines TNFα ($p<0.05$) and IL-6 ($p<0.005$). Lastly, the concentration of GM-CSF was significantly higher in the amniotic fluid of treated compared to control mice ($p<0.0001$). These studies demonstrate intrauterine GM-CSF will upregulate MMP9 and its inducer Emmprin leading to PPROM.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of treating a pregnant female subject, comprising administering to the pregnant female subject an effective amount of a Granulocyte Macrophage-Colony Stimulating Factor (GM-CSF) inhibitor, wherein the effective amount of the GM-CSF inhibitor is effective to reduce, prevent or delay preterm birth, and wherein the GM-CSF inhibitor is an anti-GM-CSF human monoclonal antibody.

2. The method of claim 1, wherein preterm birth is spontaneous preterm birth.

3. The method of claim 1, wherein the pregnant human female presents to labor and delivery with symptoms of preterm birth.

4. The method of claim 1, wherein the female subject is a pregnant human at 20 to 37 weeks of gestation.

5. The method of claim 4, wherein the pregnant human female subject is at risk of preterm birth.

6. The method of claim 5, wherein the pregnant human female subject at risk of preterm birth has a short cervical length, an infection, a placental anomaly, has had a prior cesarean delivery, has or had uterine fibroids, a connective tissue disorder, is pregnant from in vitro fertilization, diabetes, blood clotting problems, high blood pressure, vaginal bleeding, a personal history of preterm birth, a family history of preterm birth, a previous pregnancy with 18 months of the current pregnancy, a current multi-fetal pregnancy, a uterine abnormality, a cervical abnormality, is overweight before or during pregnancy, is underweight before or during pregnancy, or is carrying a fetus with known birth defects.

7. The method of claim 5, wherein the pregnant human female subject at risk of preterm birth is a human woman under the age of 20 or over the age of 35.

8. The method of claim 5, wherein the pregnant human female subject at risk of preterm birth is a human woman engaging in smoking, engaging in drinking alcohol, using illegal drugs, with limited or no healthcare during pregnancy, subject to stress, subject to long working hours with long periods of standing, or exposed to environmental pollutants.

9. The method of claim 1, further comprising checking the female subject for signs of preterm labor.

10. The method of claim 9, wherein checking the female subject for signs of preterm labor comprises a cervical exam, a transvaginal ultrasound exam, testing for amniotic fluid, or testing for fetal fibronectin.

11. The method of claim 1, further comprising administering tocolytic medicines, administering corticosteroids, performing cervical cerclage, and administering antibiotics.

12. The method of claim 1, wherein the human anti-GM-CSF antibody comprises mavrilimumab, otilimab, TJM2, lenzilumab, namilumab, gimsilumab, or PD-0360324.

* * * * *

SEQUENCE LISTING

```
<160> NUMBER OF SEQ ID NOS: 16

<210> SEQ ID NO 1
<211> LENGTH: 444
<212> TYPE: PRT
<213> ORGANISM: Artificial Sequence
<220> FEATURE:
<223> OTHER INFORMATION: Mavrilimumab heavy chain

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Glu Asn Glu Ile Val Tyr Ala Gln Arg Phe
    50                  55                  60
```

```
Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Ile Val Gly Ser Phe Ser Pro Leu Thr Leu Gly Leu Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Trp Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Trp Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 2
<211> LENGTH: 221
<212> TYPE: PRT
<213> ORGANISM: Artificial Sequence
<220> FEATURE:
<223> OTHER INFORMATION: Mavrilimumab light chain
```

<400> SEQUENCE: 2

Gln Ser Val Leu Thr Gln Pro Pro Ser Val Gly Ala Pro Gly Gln
1               5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Asp Arg Phe Ser
50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ala Thr Val Glu Ala Gly Leu
                85                  90                  95

Ser Gly Ser Val Phe Gly Gly Gly Thr Lys Leu Thr Val Leu Gly Gln
            100                 105                 110

Pro Lys Cys His Ala Ile Asn Ala Ala Pro Ser Val Thr Leu Phe Pro
        115                 120                 125

Pro Ser Ser Glu Glu Leu Gln Ala Asn Lys Ala Thr Leu Val Cys Leu
130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
            210                 215                 220

<210> SEQ ID NO 3
<211> LENGTH: 444
<212> TYPE: PRT
<213> ORGANISM: Artificial Sequence
<220> FEATURE:
<223> OTHER INFORMATION: Otilimab heavy chain

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Glu Asn Lys Tyr Ala Gly Gly Ala Thr Tyr Tyr Ala Ala
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser Ala Ser Thr Lys Gly Pro Ser Val Phe Pro Leu
        115                 120                 125

```
Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Trp Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Trp Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Trp Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 4
<211> LENGTH: 106
<212> TYPE: PRT
<213> ORGANISM: Artificial Sequence
<220> FEATURE:
<223> OTHER INFORMATION: Otilimab light chain

<400> SEQUENCE: 4

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
                20                  25                  30

Tyr Trp Tyr Gln Gln Lys Pro Gly Gln Ala Pro Val Leu Val Ile Tyr
            35                  40                  45
```

```
Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ala Trp Gly Asp Lys Gly Met Val Phe Gly
                85                  90                  95

Gly Gly Thr Lys Leu Thr Val Leu Gly Gln
                100                 105

<210> SEQ ID NO 5
<211> LENGTH: 449
<212> TYPE: PRT
<213> ORGANISM: Artificial Sequence
<220> FEATURE:
<223> OTHER INFORMATION: Lenzilumab heavy chain

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
                20                  25                  30

Tyr Ile His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Gln Arg Phe Pro Tyr Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 6
<211> LENGTH: 214
<212> TYPE: PRT
<213> ORGANISM: Artificial Sequence
<220> FEATURE:
<223> OTHER INFORMATION: Lenzilumab light chain

<400> SEQUENCE: 6

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

-continued

```
            210

<210> SEQ ID NO 7
<211> LENGTH: 445
<212> TYPE: PRT
<213> ORGANISM: Artificial Sequence
<220> FEATURE:
<223> OTHER INFORMATION: Namilumab heavy chain

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Thr Leu Ile Ser Val Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Trp Thr Val Pro Ser Ser
            180                 185                 190

Ser Leu Gly Thr Gln Thr Tyr Ile Cys Asn Val His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Trp Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Trp Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
```

```
                355                 360                 365
Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 8
<211> LENGTH: 214
<212> TYPE: PRT
<213> ORGANISM: Artificial Sequence
<220> FEATURE:
<223> OTHER INFORMATION: Namilumab light chain

<400> SEQUENCE: 8

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
                20                  25                  30

Leu Asn Trp Tyr Gln Gln Arg Pro Gly Lys Ala Pro Gln Leu Leu Ile
            35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 9
<211> LENGTH: 451
<212> TYPE: PRT
<213> ORGANISM: Artificial Sequence
<220> FEATURE:
<223> OTHER INFORMATION: Gimsilumab heavy chain

<400> SEQUENCE: 9
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Trp Met His Trp Leu Arg Gln Val Pro Gly Lys Gly Pro Val Trp Val
                35                  40                  45

Ser Arg Ile Asn Gly Ala Gly Thr Ser Ile Thr Tyr Ala Asp Ser Val
    50                  55                  60

Arg Gly Arg Phe Thr Ile Ser Arg Asp Asn Ala Asn Thr Leu Phe
65                  70                  75                  80

Leu Gln Met Asn Ser Leu Arg Ala Asp Asp Thr Ala Leu Tyr Phe Cys
                85                  90                  95

Ala Arg Ala Asn Ser Val Trp Phe Arg Gly Leu Phe Asp Tyr Trp Gly
            100                 105                 110

Gln Gly Thr Pro Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Val
```

```
                420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Gimsilumab light chain

<400> SEQUENCE: 10

Glu Ile Val Leu Thr Gln Ser Pro Val Thr Leu Ser Val Ser Pro Gly
1               5                   10                  15

Glu Arg Val Thr Leu Ser Cys Arg Ala Ser Gln Ser Val Ser Thr Asn
            20                  25                  30

Leu Ala Trp Tyr Gln Gln Lys Leu Gly Gln Gly Pro Arg Leu Leu Ile
        35                  40                  45

Tyr Gly Ala Ser Thr Arg Ala Thr Asp Ile Pro Ala Arg Phe Ser Gly
50                  55                  60

Ser Gly Ser Glu Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Trp Pro Asp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 17
<212> TYPE: PRT
<213> ORGANISM: Artificial Sequence
<220> FEATURE:
<223> OTHER INFORMATION: GM-CSF inhibitory peptide

<400> SEQUENCE: 11

Cys Gly Lys Ala Ser Ala Thr Lys Gly Lys Gly Glu Ala Thr Gly Gly
1               5                   10                  15

Cys

<210> SEQ ID NO 12
<211> LENGTH: 19
<212> TYPE: PRT
```

```
<213> ORGANISM: Artificial Sequence
<220> FEATURE:
<223> OTHER INFORMATION: GM-CSF inhibitory peptide

<400> SEQUENCE: 12

Cys Gly Thr Ala Glu Gly Lys Gly Gly Lys Gly Thr Ala Ser Ala Lys
1               5                   10                  15

Gly Gly Cys

<210> SEQ ID NO 13
<211> LENGTH: 19
<212> TYPE: PRT
<213> ORGANISM: Artificial Sequence
<220> FEATURE:
<223> OTHER INFORMATION: GM-CSF inhibitory peptide

<400> SEQUENCE: 13

Gln Pro Trp Glu His Val Asn Ala Ile Gln Glu Arg Arg Leu Leu Asn
1               5                   10                  15

Leu Ser Arg

<210> SEQ ID NO 14
<211> LENGTH: 17
<212> TYPE: PRT
<213> ORGANISM: Artificial Sequence
<220> FEATURE:
<223> OTHER INFORMATION: GM-CSF inhibitory peptide

<400> SEQUENCE: 14

Lys Asp Phe Leu Leu Val Ile Pro Phe Asp Cys Trp Glu Pro Val Gln
1               5                   10                  15

Glu

<210> SEQ ID NO 15
<211> LENGTH: 11
<212> TYPE: PRT
<213> ORGANISM: Artificial Sequence
<220> FEATURE:
<223> OTHER INFORMATION: GM-CSF inhibitory peptide

<400> SEQUENCE: 15

Phe Gln Tyr Gln Leu Asp Val His Arg Lys Asn
1               5                   10

<210> SEQ ID NO 16
<211> LENGTH: 7
<212> TYPE: PRT
<213> ORGANISM: Artificial Sequence
<220> FEATURE:
<223> OTHER INFORMATION: GM-CSF inhibitory peptide

<400> SEQUENCE: 16

Ala Asp Val Arg Ile Leu Asn
1               5
```